United States Patent [19]
Simon et al.

[11] Patent Number: 5,811,387
[45] Date of Patent: Sep. 22, 1998

[54] PEPTOID MIXTURES

[75] Inventors: Reyna J. Simon, San Francisco; Paul A. Bartlett, Kensington; Daniel V. Santi, San Francisco, all of Calif.

[73] Assignee: Chiron Corporation, Emeryville, Calif.

[21] Appl. No.: 438,746

[22] Filed: May 10, 1995

Related U.S. Application Data

[60] Division of Ser. No. 715,823, Jun. 14, 1991, abandoned, and a continuation-in-part of Ser. No. 538,339, Jun. 14, 1990, abandoned, and Ser. No. 523,791, May 15, 1990, Pat. No. 5,182,366.

[51] Int. Cl.$^6$ .................................................. A61K 38/02
[52] U.S. Cl. .................. 514/2; 514/18; 514/19; 526/318.41; 526/302; 526/314
[58] Field of Search .................................... 514/15–19, 2; 526/318.41, 302, 314

[56] References Cited

U.S. PATENT DOCUMENTS

| | | | |
|---|---|---|---|
| 3,634,364 | 1/1972 | Greenbelt et al. | 260/78 |
| 4,600,526 | 7/1986 | Gallot | 252/299.01 |
| 4,609,547 | 9/1986 | Gauman | 424/88 |
| 4,631,211 | 12/1986 | Houghten | 428/35 |

FOREIGN PATENT DOCUMENTS

| | | |
|---|---|---|
| 24 47 305 | 4/1975 | Germany. |
| 1037474 | 7/1966 | United Kingdom. |

OTHER PUBLICATIONS

Spatula Chem & Biochem Amino Acids, Pept & Proteins 267–357, 1983.

Zuckerman, Ronald et al., "Efficient Method for the Preparation of Peptoids [Oligo(N–substituted glycines)] by Submonomer Solid–Phase Synthesis", *J. Am. Chem. Soc.* (1992) vol. 114:10646–10647.

Simon, Reyna et al., "Peptoids: A Modular Approach to Drug Discovery" *Proc. Nat.l Acid. Sci. USA* (1992) vol. 89:9367–9371.

Zuckerman, Ronald et al., "Efficient Method for the Preparation of Peptoids [Oligo(N–substituted glycines)] by Submonomer Solid–Phase Synthesis", *Chemtracts–Macromolecular Chemistry* (1993) vol. 4:80–83.

Kasica, H. et al., "Electrical Condictivity of N–Substituted Polyamides", *Journal of Polymer Science Part A–1* (1968) vol. 6:1615–1623.

Cosani A. et al., "N–Substituted Poly (–amino acids). 1. Synthesis and Characterization of Poly (N–methyl–y–mehtyl L–Glutamate) and Poly (N–methyl–Y–ethyl L–glutamate)$^1$", *Macromolecules* (1978) vol. 11 No. 5; 1041–1045.

*Primary Examiner*—Cecilia J. Tsang
*Assistant Examiner*—David Lukton
*Attorney, Agent, or Firm*—Bret Field; Kenneth M. Goldman; Robert P. Blackburn

[57] ABSTRACT

Mixtures of peptoids are provided. The subject peptoid mixtures comprise at least five non-homopolymeric polymers of differing sequences having a selected number of monomer units. The polymers of the subject mixtures are preferably selected from the group of compounds of the general formula: $X_a$—(NR—$CH_2$—CO)$_n$—$X_b$, $X_a$—(O—CHR—CO)$_n$—$X_b$, $X_a$—(NH—CHR—CS)$_n$—$X_b$, $X_a$—(NOH—CHR—CO)$_n$—$X_b$, $X_a$—(O—CHR—$CH_2$—CO)$_n$—$X_b$, $X_a$—(NH—CHR—$CH_2$—$SO_2$)$_n$—Xb, Xa—(NR—$CH_2CH_2$—$SO_2$)$_n$—$X_b$, $X_a$—(NR—$CH_2CH_2$—NHCO)$_n$—$X_b$, and $X_a$—(NR—$CH_2CH_2$—OCO)$_n X_b$, where each R is independently a side chain capable of interaction with a protein, carbohydrate, lipid or nucleic acid; n is an integer from 2 to 50, inclusive; and $X_a$ and $X_b$ are each independently H, lower alkyl, lower aryl, aralkyl, lower acyl, a polypeptide of 1–100 amino acids, or an effector molecule capable of exhibiting biological activity.

7 Claims, No Drawings

PEPTOID MIXTURES

CROSS-REFERENCE TO RELATED APPLICATION

This application is a divisional of application Ser. No. 07/715,823, filed 14 Jun. 1991, now abandoned, and is a continuation-in-part of earlier filed U.S. application Ser. No. 07/538,339, filed Jun. 14, 1990, now abandoned and a CIP of U.S. application Ser. No. 07/523,791, filed May 15, 1990, now U.S. Pat. No. 5,182,366 both of which applications are incorporated herein by reference and to which applications we claim priority under 35 U.S.C. §120.

TECHNICAL FIELD

This invention relates to the fields of biochemistry and drug design. More particularly, the invention relates to modified peptides, i.e., nonnatural peptides referred to herein as peptoids, methods for preparing and isolating such peptoids wherein conventional amino acid-amino acid peptide bonds are changed so as to provide protease resistance, and conjugates formed between such peptoids and bioactive compounds.

BACKGROUND OF THE INVENTION

One may now prepare polypeptides of short and medium length by systematic, even automated, techniques. A large number of small polypeptide hormones, exhibiting potent biological activity, may be synthesized directly using automated peptide synthesizers, solid-state resin techniques, and the like. Hormones and growth factors such as epidermal growth factor, growth hormone, growth hormone releasing factor, somatostatin, vasopressin, enkephalins, endorphins, bradykinnins, and the like are all small enough to be easily accessible using current technology. Additionally, defined antigenic epitopes may be synthesized as short or medium-length polypeptides for use in vaccines. However, small polypeptides in general enjoy only a short half-life once administered, and are rapidly degraded by endogenous proteases. The therapeutic potential of such polypeptides would be dramatically increased by extension of the in vivo half-life.

In addition to increasing the half-life of peptides, other characteristics of peptides might be changed in ways which would provide useful pharmaceutically active compounds, e.g., improving binding affinity. Some of the general means contemplated for the modification of peptides are outlined in *Chemistry and Biochemistry of Amino Acids, Peptides, and Proteins-A survey of Recent Developments*, Weinstein, B., ed., Marcel Dekker, Inc., publ., New York (1983), which is incorporated herein by reference to disclose methods of modifying amino acids and peptides.

The substitution of D-amino acids for the normal L stereoisomer has been carried out in an attempt to increase half-life. The theory of this approach is that the proteolytic enzymes responsible for cleavage may be stereospecific, so that substituting a D-amino acid may render the peptide unacceptable as a cleavage substrate. However, the substitution may also destroy the peptide's activity, by rendering it unacceptable as a ligand for its normal receptor. R. M. Freidinger et al., *Pept Chem* 1987 539–48, prepared cholecystokinin cyclic peptide analogs using D-Trp. N. Sakura et al., *Pept Chem* 1987 557–60, prepared a series of neurokinin B analogs, using D-Ala, D-Trp, and D-Phe. J. Rivier et al., *Pept Chem* 1987 597–600, prepared a series of corticotropin releasing factor (CRF) peptide analogs, in which an amino acid was replaced by its D analog, and reported activities for the analogs ranging from 0.05 to 50% of the native CRF activity. Although D-isomer amino acids may be commercially available, they require either stereo-specific synthesis or a stereoresolution step for preparation. Also, since D-isomer amino acids are constrained to the opposite orientation, their use may not result in structures resembling the native peptide conformation.

Another approach to the problem has been to modify the peptide bonds that are susceptible to cleavage, for example, by replacing the amide with a saturated amine. See, for example, Skiles et al., U.S. Pat. No. 4,496,542. J. S. Kaltenbronn et al., "Proceedings of the 11th American Peptide Symposium" (ESCOM Science Publishers, The Netherlands, 1990) pp. 969–70, disclosed peptides in which all of the peptide bonds were replaced with saturated amine bonds.

Others have prepared derivatized polypeptides, typically by acetylation or alkylation. J. T. Suh et al., *Eur J Med Chem-Chim Ther* (1985) 20:563–70, disclosed Lys-Gly dipeptide derivatives for inhibition of angiotensin-converting enzyme, in which the Gly amide nitrogen was substituted with 2,3-dihydro-1H-indene. Sempuku et al., JP 58/150,562 (*Chem Abs* (1984) 100:68019b), disclosed N-substituted glycine derivatives useful for inhibition of angiotensin-converting enzyme. J. D. Young et al., "Proceedings of the 11th American Peptide Symposium" (ESCOM Science Publishers, The Netherlands, 1990) pp. 155–56, disclosed a synthesis of bradykinin, in which proline at position 7 was replaced by N-benzylglycine.

There are a number of problems with respect to using peptides as pharmaceutically active compounds. For example, the larger the peptide, the more difficult it becomes to produce commercial quantities of the peptide in sufficient purity for use as a pharmaceutically active compound. However, more importantly, with respect to the present invention, larger peptides are not particularly stable metabolically and are difficult to deliver, especially when the delivery is in convenient forms such as oral delivery systems. Further, once delivered, large peptide molecules are easily broken down by endogenous enzymes. Thus, the pharmaceutical industry still prefers to employ organic chemicals (i.e., smaller molecules which are not so difficult to synthesize and purify) rather than peptides. The number of possible organic molecules capable of interaction with any given receptor is less limited than the number of peptides meeting the same criteria. Further, organic molecules are frequently less susceptible to metabolism than are peptides, and may often be administered orally. However, it is difficult to rationally design an organic molecule for optimal activity and/or binding to a particular site.

One approach to the discovery of new pharmaceutically active organic drugs (i.e., compounds with the 3-D structure needed for binding) relies primarily on X-ray crystallography of purified receptors once the binding site is identified, organic molecules are designed to fit the available steric space and charge distribution. However, it is often difficult to obtain purified receptors, and still more difficult to crystallize the receptor so that X-ray crystallography may be applied. It is also nontrivial to devise an appropriate ligand, even after the binding site has been properly identified. Overall, it is extremely difficult to design useful pharmaceutically active compounds due to a number of factors such as the difficulty in identifying receptors, purifying and identifying the structures of compounds which bind to those receptors and thereafter synthesizing those compounds.

Another approach to the discovery of new pharmaceutically active drugs has been to synthesize a multiplicity of short peptides, followed by an assay for binding (or other) activity. R. A. Houghten, *Proc Nat Acad Sci USA* (1985) 82:5131–35, described a method for synthesizing a number of peptides by the Merrifield method. In the general Merrifield method, the C-terminal amino acid of the desired peptide is attached to a solid support, and the peptide chain is formed by sequentially adding amino acid residues, thus extending the chain to the N-terminus. The additions are performed sequentially by deprotecting the N-terminus, adding the next amino acid in protected form, deprotecting the new N-terminus, adding the next protected amino acid, etc. In Houghten's modification, C-terminal amino acids bound to supports were placed in individual polyethylene bags, and mixed and matched through the addition cycles, so that twenty bags (each containing a different C-terminal residue bound to a support) can be simultaneously deprotected and treated with the same protected amino acid. In this manner, one can obtain a set of peptides having different sequences simultaneously. The peptides are then recovered and tested for activity individually.

A modification of Houghten's approach was described by H. M. Geysen et al., *Proc Nat Acad Sci USA* (1984) 81:3998–4002 (see also WO86/06487 and WO86/00991), in which the C-terminal amino acids are supported on pins. This enabled Geysen to assay biological activity (in the form of antibody binding) without removing the peptides from the support.

Earlier methods make it possible to more quickly synthesize larger numbers of peptides than was possible previously. However, the peptide syntheses are carried out in isolated reaction conditions to produce individual peptides under each of the reaction conditions. Accordingly, these approaches do not produce mixtures of peptides containing large numbers of different peptides or peptide libraries which can be screened for the desired active peptide.

Rutter et al., PCT WO89/10931, described a method by which one can generate a large number of peptides systematically in approximately equimolar amounts, and assay the resulting library of peptides for biological activity. Rutter also disclosed using amino acids having altered side chains, such as phenylglycine, hydroxyproline, and α-aminobutyric acid. The active peptides are selected from the remainder of the library by a variety of methods, the most straightforward of which is binding to a ligand or receptor. For example, if the target peptide is to be ligand for a receptor, the library of peptides may be applied to a quantity of receptor bound to a solid support. The peptides which bind with highest affinity can then be separated from peptides with lower affinity by standard techniques. This method allows one to probe a binding site with a very large number of peptides.

Another method of producing large numbers of peptides is taught in U.S. Pat. No. 5,182,366, which is incorporated herein to disclose methods of making large numbers of peptides. This patent describes a method of preparing a mixture of peptides having a known composition and containing a peptide of a desired amino acid sequence. The method involves three essential steps. First, a given amount of a mixture of amino acyl or peptide derivatized resin is divided into a number of pools with each pool containing an equal molar amount of the resin mixture. Second, a different single amino acid is coupled to the resin mixture in each of the pools and the coupling reaction is driven to completion. The peptide mixtures in each of the pools are then mixed together to obtain a complex peptide mixture containing each peptide in retrievable and analyzable amounts. The steps can be repeated to lengthen the peptide chains and methods can be employed to retrieve the desired peptide from the mixture and carry out analyses such as the determination of the amino acid sequence. The ability to obtain mixtures with equal molar amounts of each peptide therein is dependent on the ability to accurately weigh and divide each reaction product into equal amounts and the ability to drive each reaction to completion.

Each of the above-described methods offers a method of producing one or more peptides which may have a desired biological activity. Although some of the methods may mention the use of modified amino acids, all the end products result in conventional peptide bonds. This limits applicability because only peptides are produced and if modifications are needed, substantial downstream processing is required to obtain the desired final product. Further, the peptides are subject to conventional metabolic degradation.

The present inventors postulated that there are potential nonpeptide molecules with improved protease resistance and possibly with higher affinity than the natural peptide ligand. Such nonpeptides were further postulated as less susceptible to rapid cleavage and clearance. Additionally, the present inventors postulated that such nonpeptides could be bound to pharmaceutically active organic compounds and provide conjugates which use the nonpeptide portion as biochemical targeting agents for the organic molecule bound to it.

SUMMARY OF THE INVENTION

Peptoids and peptoid libraries, methods of making such, as well as methods of isolating a bioactive peptoid from a library are disclosed. The present invention provides a systematic method for synthesizing and assaying a large number of peptide mimics or peptoids simultaneously. The compounds, referred to herein as "peptoids," may resemble conventional peptides, but contain at least two substitutes for conventional amino acids and/or peptide bonds. Preferably, the entire peptoid consists only of amino acid substitutes, i.e., does not include natural amino acids and more preferably the peptoid is bound to a bioactive compound, such as a pharmaceutically active drug. The substitutes may be any molecule suitable for standardized synthesis and incorporation. Presently preferred amino acid substitutes are N-alkylated derivatives of glycine, which are easily synthesized and incorporated into polypeptide chains. Preferred pharmaceutically active drugs include steroids and AZT.

Any monomer units which allow for the sequence specific synthesis of pools of diverse molecules are appropriate for use in producing peptoid molecules of the invention and are useful in determining the conformational space of a protein. The use of nonpeptide polymers have certain advantages. Such molecules occupy different conformational space than a peptide and as such are more resistant to the action of proteases. Further, the side chain groups can be customized for optimal binding to receptors and monomer units can be chosen for convenience of synthesis.

A primary object of the present invention is to provide a method for producing large numbers or libraries of peptoids which peptoids are polymers comprised exclusively or at least in part of amino acid substitutes.

Another object of the invention is to provide methodology for screening such peptoid libraries in order to obtain peptoids which mimic to some degree the activity of natural proteins.

An advantage of the present invention is that the monomer units of the peptoid are not limited to conventional amino acids but may include a variety of amino acid substitutes which can create a variety of three-dimensional confirmations in the resulting peptoid and thereby obtain a desired biological activity.

A feature of the present invention is that the methodology can be used to synthesize and isolate peptoids with the strongest binding affinity.

Another object of the invention is to provide peptoids which consist only of amino acid substitutes, i.e., do not include conventional amino acid monomers within the polymer chain.

Another object is to produce novel conjugates which are peptoids of the invention bound to a bioactive compound such as a pharmaceutically active drug so as to provide biochemical targeting for the drug via the enhanced binding affinity of the peptoid portion.

A feature of the present invention is that the peptoid molecules produced have improved protease resistance as compared with corresponding natural proteins.

Another feature of the present invention is that the peptoids of the present invention can be designed as to not include the sissile bond in natural proteins which bond is cleaved by natural proteases.

Another advantage of the present invention is that the peptoids and peptoid libraries of the invention can be used to explore receptor interactions, i.e., the interaction between such peptoids and the natural receptor sites.

Another object of the invention is to provide drug design methodology whereby peptoids are designed which peptides have added protease resistance as compared with peptides and have the same or stronger affinity for natural receptor sites.

Another feature of the invention is that the chemical synthesis methodology can be used in connection with solid phase polymerization techniques, making it possible to produce defined libraries and the solid phase polymerization techniques can be automated to produce compounds in commercial quantities.

Yet another feature of the invention is that the peptoids of the invention have not only different structures with respect to the bonds they contain as compared to natural peptides, but have different three-dimensional structures which structures may not be possible with conventional peptides.

These and other objects, advantages and features of the present invention will become apparent to those persons skilled in the art upon reading the details of the structure, synthesis and usage and more fully set forth below, reference being made to the accompanying general structural formulas and synthesis schemes forming a part hereof wherein like symbols refer to like molecular moieties throughout.

DETAILED DESCRIPTION OF PREFERRED EMBODIMENTS

Before the present peptoid molecules, peptoid libraries and conjugates, as well as processes for making such are described, it is to be understood that this invention is not limited to the particular amino acid substitutes, peptoids or corresponding proteins described herein as such compounds and methods may, of course, vary. It is also to be understood that the terminology used herein is for the purpose of describing particular embodiments only, and is not intended to be limiting since the scope of the present invention will be limited only by the appended claims.

The present invention includes a variety of different aspects, including novel peptoids, peptoid libraries, peptoid conjugates, processes for synthesizing such peptoids, libraries and conjugates, and processes for isolating from such libraries peptoids of desired biological activity. Further, within each of these aspects of the invention, the present invention includes a large number of specific embodiments. The essence of the invention involves providing processing technology whereby those skilled in the art can use the information disclosed and described herein in order to produce and isolate molecules which mimic the biological activity of naturally-occurring molecules but which have different chemical structures as compared to the natural molecule. The word "mimic" is used loosely, in that the molecules produced may have the same activity, greater activity, lesser activity, and/or block the effect of naturally-occurring biologically active molecules. By replacing amino acids with substitute amino acids, a peptoid is formed which peptoid can have preferred biological activity as compared to its corresponding peptide which consists only of nature amino acids.

Throughout this description and the appended claims, it must be noted that the singular forms "a," "an" and "the" include plural referents unless the context clearly dictates otherwise. Thus, for example, reference to "a peptoid" includes mixtures of such peptoids, reference to "an amino acid substitute" includes reference to mixtures of such amino acid substitutes, and reference to "the method of synthesis" includes a plurality of such methods which will occur to those skilled in the art upon reading this disclosure. In order to more particularly describe and disclose the invention, the following specific definitions are provided.

A. Definitions

"Amino acid" is used in a more restricted sense than any compound which includes $NH_2$—R—COOH in its structure. Amino acid means any of the twenty naturally occurring alpha-amino acids.

Monomer units in the form of "amino acid substitutes" make up polymer or "peptoid" molecules of the present invention which molecules have certain characteristics. A "peptoid" is a polymer made up, at least in part, of monomer units of "amino acid substitutes" which substitutes are any molecule other than an amino acid but which serves in the peptoid polymer to mimic an amino acid. A peptoid of the invention: (1) includes a plurality of monomer units; (2) provides a desired biochemical activity, e.g., mimics a natural protein, blocks a natural receptor site, generates a desired immune response; and (3) has at least two monomer units which are not conventional amino acids. A peptoid of the invention preferably (4) includes 2 to 50 monomer units (more preferably 5 to 10 monomer units; (5) presents a three-dimensional conformation biologically compatible with a natural protein or portion thereof, i.e., the peptoids have the same or greater affinity for natural receptors as do natural peptides; and (6) includes less than 50% of its monomer units as amino acids (more preferably no amino acids). Particularly preferred monomer units are N-alkylated derivatives of glycine. Peptoids are produced by linking the "amino acid substitutes" into a linear chain with amino acids and/or other amino acid substitutes. The links may include, without limitation, peptide bonds, esters, ethers, amines, phosphates, sulfates, sulfites, thioethers, thioesters, and aliphatic bonds. Exemplary amino acid substitutes include N-substituted glycine, N-substituted alanine, N-substituted D-alanine, substituted hydroxy acids such as hydroxyacetic acid, 2-hydroxypropanoic acid, 3-hydroxypropanoic acid, 3-phenyl-2-hydroxypropanoic acid and the like. A peptoid may comprise amino acid substitutes using more than one type of link provided the chemistry for the reaction schemes are compatible and encompassed generally by the reactions described herein.

The phrase "compound of Formula I" refers to a peptide analog having the following structure:

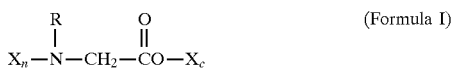

(Formula I)

wherein:

R is alkyl of 2–6 carbon atoms, haloalkyl of 1–6 carbon atoms where halo is F, Cl, Br, or I, alkenyl of 2–6 carbon atoms, alkynyl of 2–6 carbon atoms, cycloalkyl of 3–8 carbon atoms, aryl of 6–10 carbon atoms, arylalkyl of 7–12 carbon atoms, arylalkyl of 7–12 carbon atoms substituted with 1–3 radicals independently selected from halo and nitro and hydroxy, aminoalkyl of 1–6 carbon atoms, hydroxyalkyl of 1–6 carbon atoms, carboxyalkyl of 2–6 carbon atoms, carboalkoxy-alkyl of 3–10 carbon atoms, carbamyl, carbamylalkyl of 2–6 carbon atoms, guanidino, guanidinoalkyl of 1–6 carbon atoms, mercapto, mercaptoalkyl of 1–6 carbon atoms, alkylthio of 1–6 carbon atoms, alkylthioalkyl of 2–10 carbon atoms, imidazolyl, imidazolylalkyl of 4–10 carbon atoms, indolyl, or indolylalkyl of 9–15 carbon atoms;

$X_n$ and $X_c$ are each independently H, a peptide chain of 1–50 amino acids, or another radical of Formula I; wherein if $X_n$ is H then $X_c$ is a chain of at least 2 amino acids or a radical of Formula I, and if $X_c$ is H then $X_n$ is a chain of at least 1 amino acid or a radical of Formula I; and salts thereof.

An important aspect of the invention is drawn to polypeptides comprising N-substituted glycine analogs which resemble naturally-occurring amino acids (i.e., Ala, Cys, Asp, Glu, Glu, Phe, His, Ile, Lys, Leu, Met, Asn, Gln, Arg, Ser, Thr, Val, Trp, and Tyr). The radicals $X_n$ and $X_c$ are either chains of conventional amino acids, chains of one or more N-substituted glycine analogs, or chains in which conventional amino acids and N-substituted glycine analogs are interspersed.

The presently preferred N-substituted glycine analogs are those in which R is ethyl, prop-1-yl, prop-2-yl, 1-methylprop-1-yl, 2-methylprop-1-yl, benzyl, 4-hydroxybenzyl, 2-hydroxyethyl, mercaptoethyl, 2-aminoethyl, 3-aminopropyl, 4-aminobutyl, 2-methylthioeth-1-yl, carboxymethyl, 2-carboxyethyl, carbamylmethyl, 2-carbamylethyl, 3-guanidinoprop-1-yl, imidazolylmethyl, or indol-3-yl-ethyl, particularly where R is 2-methylpropyl, benzyl, 2-hydroxyethyl, 2-aminoethyl, or carboxymethyl. The "resemblance" between amino acid and substitute need not be exact. For example, one may replace lysine with compounds of formula I in which R is aminomethyl, 2-aminoethyl, 3-aminopropyl, 4-aminobutyl, 5-aminopentyl, or 6-aminohexyl. Serine may be replaced with hydroxymethyl, 2-hydroxyethyl, 3-hydroxypropyl, 2-hydroxypropyl, and the like. In general, a conventional amino acid may be replaced with an N-substituted glycine analog having a sidechain of similar character, e.g., hydrophobic, hydrophilic, polar, nonpolar, aromatic, etc.

A "compound of formula II" has the following structure:

(Formula II)

where R is as defined above, and L is a divalent radical equivalent in length to an amino acid.

The term "monomer" refers to a molecule which may be linked to other monomers to form a peptoid. Monomers include amino acid substitutes, which may include N- and/or C-terminal modifications to facilitate linking, for example, leaving or activating groups.

The term "N-substituted glycine analog" refers to compounds of the formula $RNH-CH_2-COOH$, where R is as defined above. The salts and esters of these compounds, as well as compounds of the formula bearing standard protecting groups (e.g., Fmoc, t-Boc, and the like) are also considered within the definition of "monomer" and "N-substituted glycine analog" unless otherwise specified.

The terms "conventional" and "naturally occurring" as applied to peptides herein refer to polypeptides, also referred to as proteins, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity related to the biological activity of the natural protein. The elicited activity may be the same as, greater than or less than that of the natural protein, i.e., provide enhanced and/or blocking effects. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. Thus, the following pairs of peptides would be considered "corresponding":

Ia: Asp-Arg-Val-Tyr-Ile-His-Pro-Phe (Angiotensin II)

Ib: Asp-Arg-Val*-Tyr-Ile*-His-Pro-Phe

IIa: Arg-Pro-Pro-Gly-Phe-Ser-Pro-Phe-Arg (Bradykinin)

IIb: Arg-Pro-Pro-Gly-Phe*-Ser*-Pro-Phe*-Arg

IIIa: Gly-Gly-Phe-Met-Thr-Ser-Glu-Lys-Ser-Gln-Thr-Pro-Leu-Val-Thr (β-Endorphin)

IIIb: Gly-Gly-Phe*-Met-Ser*-Ser-Glu-Lys*-Ser-Gln-Ser*-Pro-Leu-Val*-Thr

In these examples, "Val*" refers to N-(prop-2-yl)glycine, "Phe*" refers to N-benzylglycine, "Ser*" refers to N-(2-hydroxyethyl)glycine, "Leu*" refers to N-(2-methylprop-1-yl)glycine. and "Ile*" refers to N-(i-methylprop-1-yl) glycine.

The correspondence need not be exact: for example, N-(2-hydroxyethyl)glycine may substitute for Ser, Thr, Cys, and Met;. N-(2-methylprop-1-yl)glycine may substitute for Val, Leu, and Ile. Note in IIIa and IIIb above that Ser* is used to substitute for Thr and Ser, despite the structural differences: the sidechain in Ser* is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

The term "conjugate" is a peptoid of the invention bound covalently to a pharmaceutically active drug or drugs. The peptoid may be synthesized for an affinity to a particular bacterial and then bound to an antibacterial agent such as trimethoprim. As another example, a peptoid is a modified peptide with affinity for some receptor of the AIDS virus which peptoid is bound to AZT. The peptoid portion of the conjugate is designed to resist degradation while having a high affinity for a particular receptor. Thus, the peptoid provides for a biochemical targeting or delivery system for the drug it is bound to. Libraries of peptoids are screened for their affinity to a desired target and when the peptoid with the highest affinity is found it is bound to a drug to form a conjugate.

The term "effector compound" includes any compound which binds to a biological receptor site and effects a biochemical event after so binding. Thus, effector compound includes pharmaceutical drug as well as insecticides, but is not limited to either.

B. General Method

In order to produce the peptoids of the invention it is first necessary to have or synthesize the monomer units which will make up the peptoids. These monomer units may include conventional amino acids but more preferably include substitute amino acids. The details of such substituted amino acids are described further below. Once the monomer units of the invention are provided the units are linked together to provide polymers, which polymers include at least some substitute amino acids and thus are peptoids. An important aspect of the present invention is that the monomer units are combined with each other in such a manner so as to provide a library of peptoids each with different amino acid sequences. This library of peptoids is produced in a single reaction vessel which can then be screened in order to extract a peptoid of desired biological activity.

In addition to producing an entire peptoid and peptoid library using individual starting monomer units it is possible to produce different peptoids by beginning with a polymer chain such as a chain of natural amino acids and then linking additional amino acids and substitute amino acids to the chain to produce a peptoid. Monomers such as amino acids and substitute amino acids are first protected and then linked into a polymer chain using any suitable coupling technique. For example, the monomer units such as the substitute amino acids may be first protected and then reacted with the unprotected reaction site of a chain using solid-phase synthetic techniques after the chain has been immobilized on a resin.

The methodology for producing the libraries of peptoids is described within PCT published application WO 89/10931, which application is incorporated herein by reference. This methodology is of particular importance in that it is capable of generating mixtures of peptides (or when used with the present invention produces peptoids) wherein each different peptide (or peptoid) is present in the mixture in substantially equally molar amounts and/or in predictable and retrievable amounts.

In general, the methodology involves preparing libraries or large mixtures of peptides. In accordance with the present invention this methodology allows for the production of libraries of peptoids. More specifically, applicant's method involves preparing mixtures of distinct, unique and different peptoids in the same reaction vessel. That is, the peptides within the reaction vessel are different from one another and each of the peptides in the reaction vessel is present in retrievable and analyzable amounts. The method is carried out by combining and reacting activated monomer units such as activated amino acids or activated substituted amino acids with acceptor monomer units or an acceptor peptide. The activated monomer units are provided in concentrations relative to each other based on their relative coupling constants. The coupling constants for conventional amino acids are known and by using techniques described in the literature and WO89/10931 can be calculated for any given substitute amino acids. By combining the reactants in this manner the resulting mixture of peptoids will contain each reaction product or peptoid in a predictable and defined amount and in an amount sufficient such that the peptoids can be retrieved and analyzed. The resulting amounts of each of the peptoids is predictable in that the reaction rate constants are known and the reactants are being added with each other based on the reaction rate constants. The length of the peptoid chain can be continually increased by repeating this procedure time and time again, wherein each time the mixture of activated monomer units is added and reacted with the acceptor monomer units or peptide in amounts based on the reaction rate constants of the activated monomer units.

In accordance with another general aspect of the invention, individual peptoids are produced using methodology such as solid-phase synthetic techniques after immobilizing one terminal monomer unit on a resin. The techniques are carried out in order to produce novel peptoids which include substituted amino acids. The peptoids have improved metabolic stability. The substituted amino acids may include side-chains which may include active reaction sites or which may be modified to include reaction sites, that is, acceptor sites. These acceptor sites can then be covalently bound to other molecules such as pharmaceutically active compounds to form conjugates. In this manner, the peptoids of the invention can be used as chemical delivery systems. When the conjugate is administered, the peptoid will bind to a specific receptor site and the pharmaceutically-active compound bound to the peptoid will be delivered to the desired site. Thus, conjugates of the invention include peptoid units wherein one or more of the substituted amino acids within the peptoid has a pharmaceutically active compound attached thereto.

Amino Acid Substitutes

As indicated above the peptoids of the invention can be produced using amino acids as the monomer units or amino acid substitutes. Examples of different modifications in amino acids which can be carried out in order to obtain the amino acid substitutes used in the invention are put forth below in Table 1.

TABLE 1

| Type of Modification | Isosteric | Enzyze Resistance | H-Bonding | Chiral Monomer |
|---|---|---|---|---|
| I. Peptides | | | | |
| II. N-alkylation | + | +++ | + | No |
| III. α-Ester | +++ | + | +++ | Yes |
| IV. Thioamide | +++ | ++ | + | Yes |
| V. N-hydroxylation | + | +++ | + | Yes |
| VI. β-Ester | + | ++ | ++ | Yes |
| VII. Sulfonamide | + | ++ | ++ | Yes |
| VIII. Sulfonamide-N | + | ++ | ++ | No |
| IX. Urea | + | ++ | ++ | No |
| X. Urethane | + | ++ | ++ | No |

Items II, III, IV and IX are taken from Spatola, A., "Peptide Backbone Modifications: . . . " in Chemistry and Biochemistry of Amino Acids, Peptides, and Proteins (1983) 7:267, B. Weinstein ed. (incorporated herein by reference). The + refers to the extent to which replacement is characterized by the given property: + = minimal, ++ = partial, +++ = substantial.

As can be seen from the table, modifications can significantly alter the properties of the molecules, particularly with respect to enzymatic hydrolysis. From a synthetic standpoint, chiral starting materials can be problematic. Even if they are easily synthesized, the fidelity of the subsequent coupling reactions needs to be addressed. Each substitute amino acid structure will be discussed briefly below and can be compared to the amino acid structure in a polypeptide.

I. POLYPEPTIDE

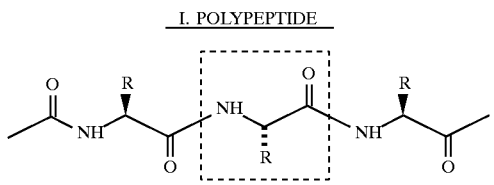

The individual monomer units or substitute peptides such as those described below can be combined together in any manner. However, it is most preferable to combine the monomer units using methodology such as disclosed within published PCT application WO89/10931 in order to obtain large libraries of different peptoids, which libraries can then be screened to find one or more peptoids which has a particular characteristic such as a high affinity for a particular receptor site. Although the substitute amino acids put forth below are examples of preferred substitute amino acids which can be used in connection with producing peptoids of the invention, it should be noted that any monomer unit can be used which would allow for sequence specific synthesis of pools of diverse molecules. Any such monomer unit would be suitable for use in connection with the present invention in that such units would make it possible to search and screen for particular conformational shapes which have affinity for particular receptor sites. The use of nonpeptide polymers is believed to have particular advantages over conventional peptides in that such peptoids would occupy different conformational configurations in space and should provide resistance to the action of proteases, which feature would be particularly important to designing conjugates wherein the peptoid portion would have a desirably long half-life. Further, substitute amino acids could be designed so as to provide for molecules which are generally easier to synthesize than conventional peptides might be.

II. POLY N-ALKYLATED GLYCINE

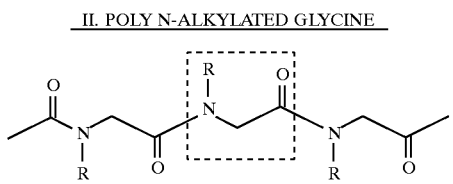

II. N-alkylated glycines: The main advantages of this system are the ease of synthesis of the properly protected achiral monomers and the vast literature of peptides concerning the synthesis and characterization of the closely related peptide polymers. The main disadvantage is the decrease in properties dependent on the availability of amide protons for hydrogen bonding, such as solubility in aqueous systems, conformational rigidity, secondary structure, etc. It is pointed out that N-alkylated glycines are a preferred class of N-substituted glycines which can be used in connection with the present invention. Thus other chemically compatible groups other than R=alkyl may be used. Further, the substitutions may be made on the nineteen other natural amino acids.

III. α-POLYESTER

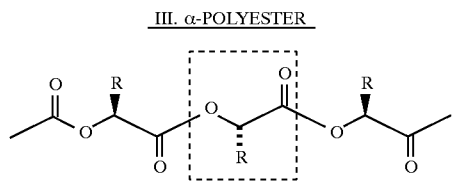

III. α-Esters: Polyesters are one of the closest relatives to the normal peptide bonds. The advantage is the close similarity, however, this can also be a drawback since proteolytic enzymes are known to recognize esters or even prefer esters as their substrates. α-Polyesters are prepared from chiral α-hydroxy acids in which there has been considerable synthetic interest (Chan, P. C., et al., *Tetrahedron Lett* (1990) 31:1985). In a stepwise fashion, polymers can be assembled much as polyamides are prepared.

IV. POLYTHIOAMIDE

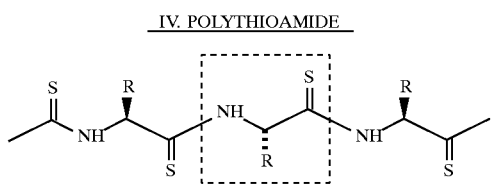

IV. Thioamides: The thioamide is also rather similar to the normal peptide. According to Clausen, K., et al., *J Chem Soc Perkin Trans* (1984) 1:785, until 1984 there had been only limited reports of the thioamide replacement for a peptide bond which they attribute to the difficulty in synthesis. He describes the synthesis and use of a protected thioamide precursor using Lawessons's reagent. Also, a recent report (*Tetrahedron Lett* (1990) 31:23) describes the conversion of a peptide bond to a thioamide using the same reagent.

V. POLYHYDROXYAMATE

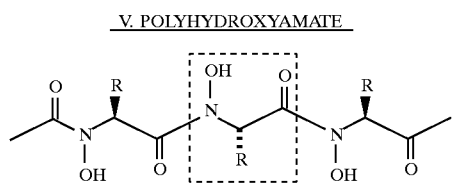

V. N-hydroxy amino acids: The advantages are the decreased sensitivity to enzyme hydrolysis and H-bonding ability due to the added hydroxyl group. Kolasa et al. has described the synthesis of N-hydroxypeptides (Kolasa, T., et al, *Tetrahedron* (1977) 33:3285).

VI. β-POLYESTER

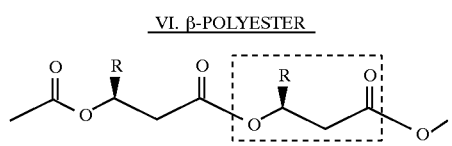

VI. β-Ester: This is an example of a homologue of the α-ester. Presumably the different spacing will confer some special properties such as increased resistance to enzyme hydrolysis or novel conformational flexibility. The appropriate starting materials are readily synthesized (Elliott, J., et al., *Tetrahedron Lett* (1985) 26:2535, and *Tetrahedron Lett* (1974) 15:1333.

VII. POLYSULFONAMIDE

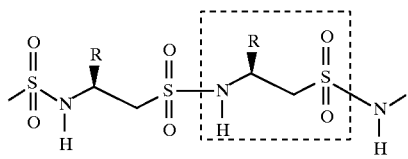

VIII. POLYSULFONAMIDE N-ALKYLATED

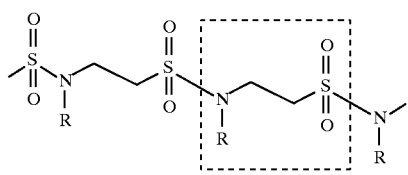

VII. and VIII. Sulfonamides: The two sulfonamides differ by the positioning of the R group. According to Frankel and Moses (Frankel, M., et al., *Tetrahedron* (1960) 9:289), the peptide analog, i.e., the 1,4 substituted polymer is not stable under their condensation conditions. Compounds of the type VII are readily obtained from chiral β-amino alcohols (Kokotos, G., *Synthesis* (1990) 299) while those of the type VIII are achiral and easily synthesized.

IX. POLYUREA

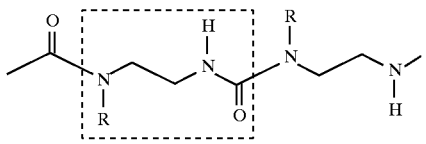

IX. Ureas: Ureas are also conveniently synthesized from carboxylic acids and amines using the reagent diphenylphosphoryl azide, DPPA (Shiori, T., et al., *J Am Chem Soc* (1972) 94:6203, and Bartlett, P., et al., *Synthesis* (1989) 542). Previously prepared peptides with a single urea replacement had properties similar to the starting peptide (see reference 1, p. 231). Additionally, since there is still an amide proton available for H-bonding, the solubility properties may be better than for N-alkylated glycines.

X. POLYURETHANE

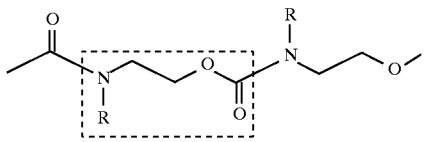

X. Urethanes: The structure of a urethane is slightly different than that of a urea and would presumably have altered properties. Aqueous solubility may be somewhat reduced since the amide proton is removed. The polymers could be prepared via simple chemistry.

There are numerous other polymer systems which could be employed for the purpose of searching conformational space. Most notable are the phosphorous derived polymers with phosphonamides as one example (Yamauchi, K., et al., *Bull Chem Soc Japan* (1972) 45:2528). Polyamines (*Tetrahedron Lett* (1990) 31:23, and Kaltenbronn, J. S., et al., in *Proceedings of the Eleventh American Peptide Symposium* (1989) 969, J. Rivier, ed.), polyalkanes, polyketones (Almquist, G., et al., *J Med Chem* (1984) 27:115, polythioethers, polysulfoxides (Spatola, A., et al., *Biopolymers* (1986) 25:S229) and polyethers would be less suitable for our purposes due to either difficulty in synthesis or predictably poor properties (e.g., polyamines would carry a positive charge at every junction and require double amine protection during synthesis). In summary, several alternatives to N-alkylated glycine polymers of which libraries could be constructed have been described.

Preparation of α-polyesters Using Chiral α-hydroxy Acids as Building Blocks

The α-polyester structures can be prepared by using chemical synthesis technology known to those skilled in the art. For details of the reaction, see Brewster, P., et al., *Nature*, (1990) 166:179, incorporated herein by reference. An alternative methods for producing similar structures is disclosed in Chan, P. C., and Chong, J. M., *Tetrahedron Lett.* (1990) 1985, which publication is incorporated herein by reference in its entirety. Further, it is pointed out that various publications cited within the Chan et al. publication describe techniques for synthesizing chiral α-hydroxy acids.

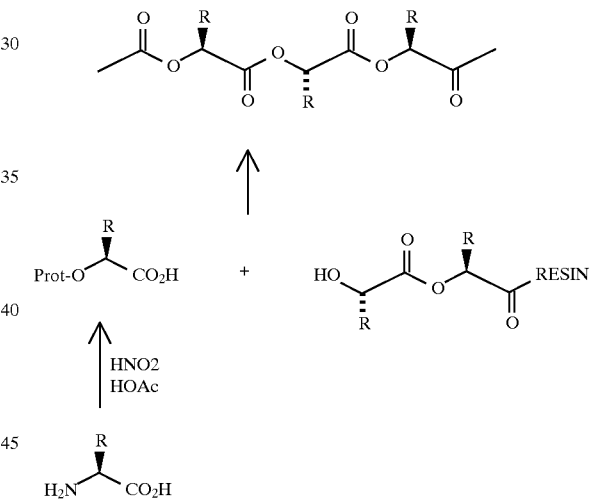

Preparation of Polythioamides Using Chiral α-amino Acids as Building Blocks

Polythioamide structures such as those shown below can be synthesized using techniques such as those described within Clausen, K., et al., *J. Chem. Soc. Perkin Trans. I* (1984) 785, and *Tetrahedron Lett.* (1990) 31:23, which publications are incorporated herein by reference.

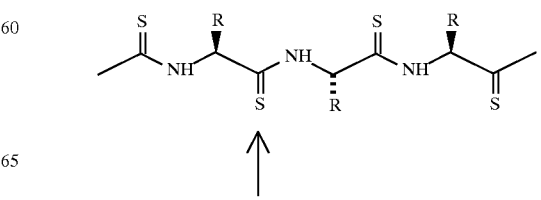

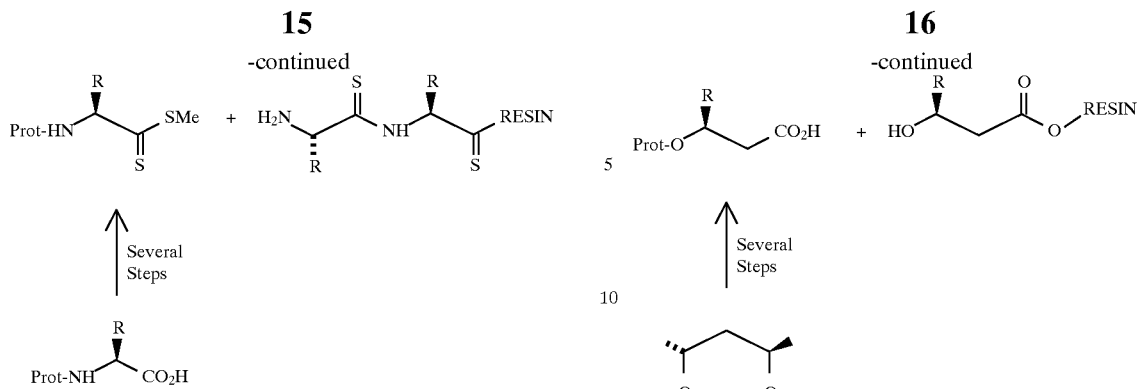

Preparation of Polyhydroxymates Using Chiral α-amino Acids as Building Blocks Polyhydroxymates, as described below, can be synthesized using techniques as disclosed within Kolasa, T., and Chimiak, A., *Tetrahedron* (1977) 33:3285, which publication is incorporated herein by reference. It is also noted that references cited within Kolasa disclose and describe chemical techniques for synthesizing N-hydroxy amino acids which can be used in a peptide synthesis.

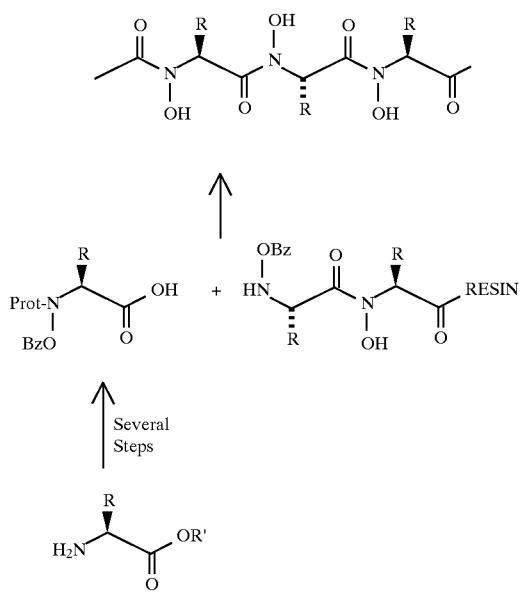

Preparation of β-polyesters Using Chiral β-hydroxy Acids as Building Blocks

β-polyesters can be synthesized using a synthesis protocol as outlined below. For additional details of such synthesis of chiral β-amino alcohols, reference is made to Elliott, J. D., et al., *Tetrahedron Lett.* (1985) 26:2535, and *Tetrahedron Lett.* (1974) 15:1333, both of which publications are incorporated herein by reference.

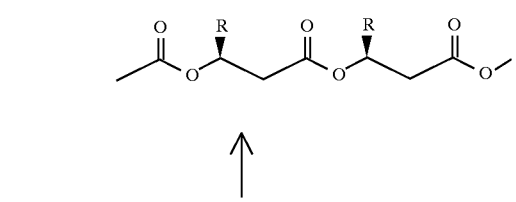

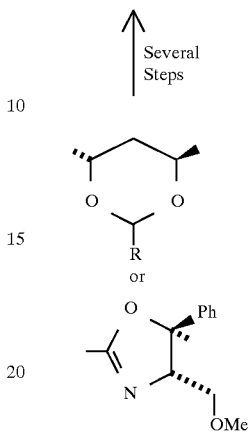

Preparation of Polysulfonamides Using Chiral β-amino Sulfonic Acids as Building Blocks Polysulfonamides can be synthesized using the reaction scheme shown below. The chiral β-amino acids have been described within Kokotos, G., *Synthesis* (1990) 299, incorporated herein by reference.

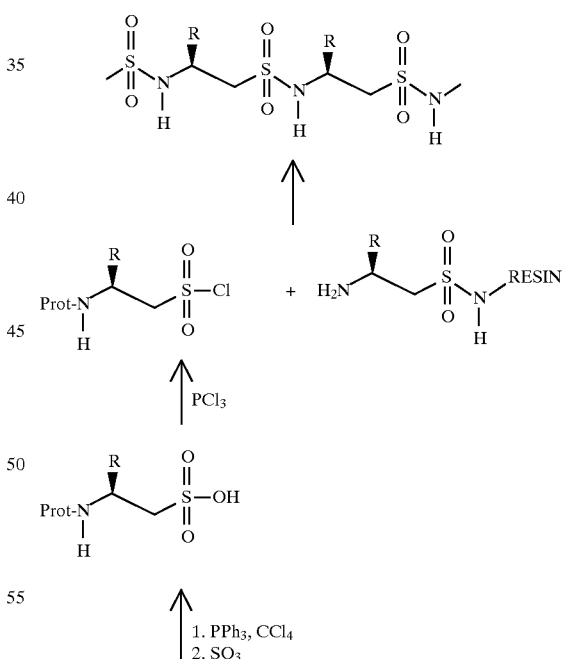

Preparation of N-alkylated Polysulfonamides Using Achiral β-amino Sulfonic Acids as Building Blocks

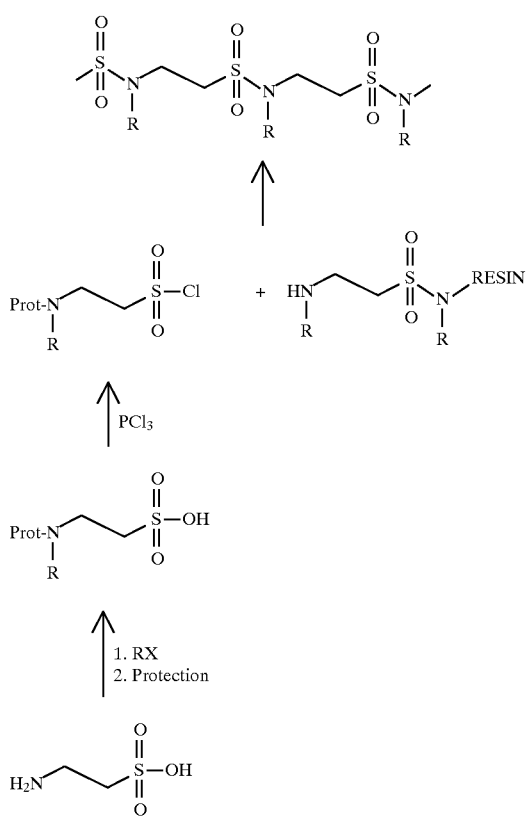

Preparation of Polyureas Using Achiral β-amino Acids as Building Blocks

Polyureas can be synthesized using techniques such as those described within Shiori, T., et al., *J. Am. Chem. Soc.* (1972) 94:6302, and Scholtz, J., and Bartlett, P., *Synthesis* (1989) 542, both of which publications are incorporated herein by reference.

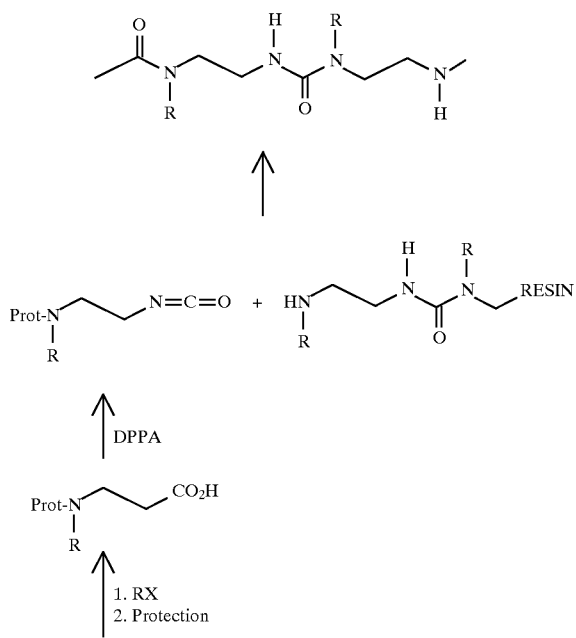

Preparation of Polyurethanes Using Achiral β-amino Alcohols as Building Blocks Polyurethanes can be synthesized using the reaction scheme put forth below.

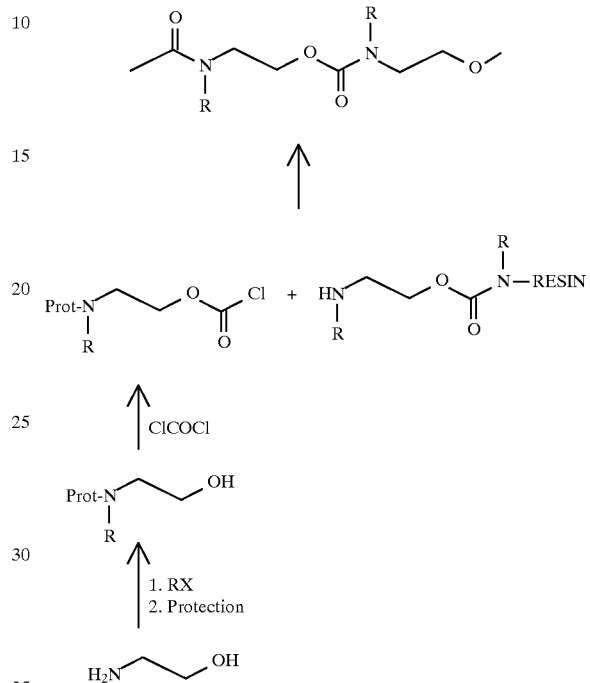

Individual N-substituted glycine analogs are known in the art, and may be prepared by known methods. See, for example, Sempuku et al., JP 58/150,562 (*Chem Abs* (1984) 100:68019b); Richard et al., U.S. Pat. No. 4,684,483 (incorporated herein by reference); and Pulwer et al., EPO 187,130.

Several N-substituted glycine derivatives are available from commercial sources. For example, N-benzylglycine is available from Aldrich Chemical Co. (Milwaukee, Wis.) as the ethyl ester. The ester is hydrolyzed in KOH/MeOH, then protonated in HCl to yield N-benzylglycine. This may then be protected with Fmoc (fluorenylmethoxycarbonyl) by treatment with Fmoc-Cl in aqueous dioxane at high pH (about 10).

Other N-substituted glycine analogs are synthesized by simple chemical procedures. N-isobutylglycine may be prepared by reacting excess 2-methylpropylamine with a haloacetic acid.

N-(2-aminoethyl)glycine may be prepared by reacting excess 1,2-diaminoethane with a haloacetic acid and purifying on Dowex-1® (OH form), eluting with acetic acid. The unprotected amine is protected with t-butoxycarbonyl (t-Boc) using conventional techniques at pH 11.2, followed by protection of the secondary amine with Fmoc.

N-(2-hydroxyethyl)glycine may be prepared by reacting excess 2-aminoethanol with haloacetic acid and purifying on Dowex-1® (OH form), eluting with acetic acid. The amine nitrogen is then protected with Fmoc. Next, the acid group is esterified with methanol under acidic conditions. The methyl ester is then treated with isobutylene to form the t-butyl ether. Then, the methyl ester is hydrolyzed using porcine liver esterase in phosphate buffer at pH 8.0, to provide a protected N-substituted glycine analog in a form suitable for peptide synthesis. As an alternative to the above, the Fmoc-hydroxyethylglycine is treated with t-butyldiphenylsilylchloride in DMF and imidazole to give a silyl-protected alcohol.

N-(carboxymethyl)glycine may be prepared by reacting glycine t-butyl ester with 2-haloacetate in aqueous solution. The product may be protected directly by addition of Fmoc. As an alternative, the N-(carboxymethyl) glycine may be prepared by mixing glycine t-butyl ester, glyoxylic acid and palladium on charcoal under an atmosphere of hydrogen in water at pH 6. The compound is then treated with FMOC in the usual manner.

Once the monomers have been synthesized, they may be coupled with other monomers and/or conventional amino acids to form polypeptide analogs using standard peptide chemistry. For example, an Fmoc-protected monomer (N-substituted glycine or conventional amino acid) may be immobilized on a suitable resin (e.g., HMP) by reaction with benzotriazol-1-yloxy-tris(dimethylamino)phosphonium hexafluorophosphate ("BOP") or a carbodiimide (for example, dicyclohexylcarbodiimide) under basic conditions (e.g., pH≧9) in a suitable solvent. The Fmoc protecting group is removed by treatment with piperidine. Each additional monomer is then attached sequentially using BOP or a carbodiimide, until the entire sequence has been constructed. The completed chain is then detached from the resin and the sidechain deprotected by treating with trifluoroacetic acid (TFA).

Alternatively, one may connect N-substituted glycine analogs to the ends of peptides produced by other methods, for example, by recombinant expression or isolation from natural sources. Further, N-substituted glycine analogs may be inserted within the sequence of such peptides by cleaving the peptide at the desired position, attaching an N-substituted glycine analog, and reattaching the remainder of the molecule or a chemically-synthesized replacement.

The peptides of the invention will have at least one monomer, preferably at least two, and more preferably three or more. If there is only one monomer, it is preferred that the analog not be N-benzylglycine. Using the monomers of the invention, one may construct peptides containing only N-substituted glycine analogs or other monomers. By varying the sidechains (e.g., by extending or shortening a methylene chain), one can obtain a family of peptide analogs useful for probing the binding interactions between particular peptides and proteins, for example, the interaction between peptide growth factors and their receptors.

Peptides suitable for modelling according to the invention include adrenocorticotropic hormone, angiotensin I–III, bradykinins, dynorphins, endorphins, enkephalins, gastrin and gastrin-related peptides, bombesins, cholecystokinins, galanin, gastric inhibitory peptides, gastrin-releasing peptide, motilin, neuropeptide Y, pancreastatin, secretin, vasoactive intestinal peptide, growth hormone, growth hormone releasing factor (GRF), luteinizing hormone releasing hormone (LHRH), melanocyte stimulating hormones (MSH), neurotensins, nerve growth factor (NGF), oxytocin, vasopressin, somatostatin, substance P, atrial natriuretic peptide (ANP), corticotropin releasing factors, epidermal growth factor, insulin, thymosin, calcitonin, urotensin, and the like. Other suitable peptides include fragments of larger proteins, such as tissue plasminogen activator (tPA) and erythropoietin (EPO), and antigenic epitopes derived from infectious organisms, for example, peptides derived from malarial circumsporozoite antigens or chlamydia major outer membrane protein antigens. However, the peptides of the invention need not be patterned directly on any known peptide, but may be constructed "at random" and tested in general screening assays for any serendipitous biological activity. In general, any peptide having at least 3 amino acids, preferably 4 or more, and most preferably 6 or more amino acids will benefit from the method of the invention. There is no theoretical upper limit to the peptide size; however, it is presently preferred to select peptides having no more than 500 amino acids, preferably 200 or fewer, more preferably 100 or fewer, and most preferably about 10 to about 50.

Peptoid Libraries

For probing the binding area of a protein or other molecule, it is generally preferred to create a library of peptoids having a variety of sequences. By applying the techniques taught in Rutter, supra, to synthesis of a collection of peptoids using nonconventional amino acids, one may prepare a large group of compounds for screening. For example, one may prepare a library of N-substituted glycine derivatives modelled on a known peptide for analysis of its receptor binding site. If a known peptide has, for example, the sequence Phe-Ala-Ser-Ser (FASS), one could prepare a library of peptoids having the following sequences:

Phe, N-methylglycine, N-(2-hydroxyethyl)glycine, N-(2-hydroxyethyl)glycine;

N-benzylglycine, N-ethylglycine N-(2-hydroxyethyl)glycine, N-(2-hydroxyethyl)glycine;

N-benzylglycine, N-methylglycine, N-(3-hydroxypropyl) glycine, N-(2-hydroxyethyl)glycine;

N-benzylglycine, N-ethylglycine, N-(2-hydroxyethyl)glycine, N-(3-hydroxypropyl)glycine;

N-(2-phenylethyl)glycine, N-methylglycine, N-(2-hydroxyethyl)glycine, N-(2-hydroxyethyl)glycine;

N-(2-phenylethyl)glycine, N-ethylglycine, N-(2-hydroxyethyl)glycine, N-(2-hydroxyethyl)glycine;

N-(1-phenylethyl)glycine, N-methylglycine, N-(3-hydroxypropyl)glycine, N-(2-hydroxyethyl) glycine;

N-(3-(3-methylphenyl)propyl)glycine, N-ethylglycine, N-(2-hydroxyethyl)glycine, N-(3-hydroxypropyl)glycine; etc.

Depending upon the set of monomers available, the library may be larger or smaller. This library would be useful for identifying peptoid analogs to the FASS peptide which bind with equivalent or higher (or lower, if desired) affinity to the FASS peptide's receptor. For example, if the hypothetical peptide bound to a known cell-surface receptor, one could plate a culture of the appropriate cells, apply the library under conditions conducive to binding, and allow binding to occur.

Nonbinding peptoids in the library are removed by washing. If a large number of peptoids exhibit high binding affinity, the binding conditions may be altered so that only the highest affinity peptoids remain bound. The resulting selected peptoids may then be identified by standard analytical techniques. Similarly, if the receptor has been isolated in active form, it may be fixed to a solid support and used to separate the highest-binding peptoids by methods akin to chromatography. Peptides which bind DNA sequences may similarly be separated using solid-phase DNA probes. The peptoids identified should be superior to the native peptide both in its activity and in its bioavailability (as incorporation of nonpeptide bonds reduces susceptibility to enzymatic degradation).

If the sequence of the native peptide is unknown, for example, where only a supernatant factor having a give activity has been identified, one may still employ the method of the invention by simply constructing a larger library. Absent clues as to the structural configuration of the peptide or epitope, a "universal" library having a large range of sequence variations is most useful.

Synthesis of Peptoid/Drug Conjugates

A mixture of peptoids is synthesized in accordance with the methodology disclosed herein. The resulting mixture includes a large number of different peptoids with each peptoid being present in a substantially equal molar amount. In general, the peptoids within the mixture are covalently bound to a given pharmaceutically active drug. The conjugates can then be tested for their affinity to a receptor site. After determining which conjugate has the strongest affinity for the particular receptor site, that conjugate is then individually synthesized. As an example, a mixture of peptoids is synthesized and the individual peptoids within the mixture are covalently bound to the drug trimethoprim. Trimethoprim is a potent inhibitor of bacterial dihydrofolate reductases. Accordingly, trimethoprim is used as an anti-infective agent. Trimethoprim includes three methoxy groups which can be substituted with a variety of groups and still retain activity as a dihydrofolate reductase inhibitor. Accordingly, trimethoprim is a particularly adaptable drug for use in connection with the present invention. The substitution pattern of trimethoprim determines specificity, and the groups must be ethers. Thus, if a mixture of peptoids is synthesized with an appropriate linker to the drug, a random screen can be performed with the selection criteria determined by the specificity one wishes to obtain, thereby optimizing a ligand with known activity. For example, mixtures can be used to screen for drugs of enhanced selectivity for a particular dihydrofolate reductase.

The particular chemistry of forming a conjugate between a peptoid and trimethoprim is carried out by first forming the peptoid mixture. Thereafter, the process involves derivatizing the N-terminus of the peptoids within the mixture with the appropriately activated drug through an amid linkage. The reaction is shown as follows:

{Drug}-(CH$_2$)$_x$—COOR'+HN-Mixture-CONH$_2$→

{Drug}-(CH$_2$)$_x$—CO—N-Mixture-CONH$_2$

The structural formulas of the trimethoprim drug and the conjugate which might be formed with a peptoid of the invention is shown below:

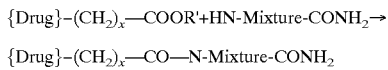
Trimethoprim

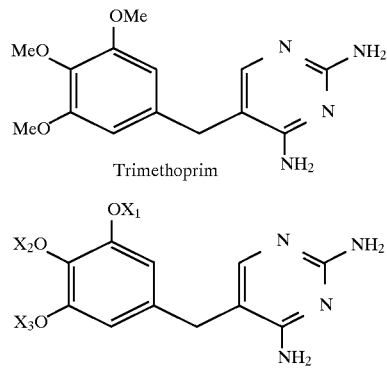

X$_1$=(CH$_2$)$_x$CON-(peptoid mixture), X$_2$=X$_3$=Me
X$_1$=X$_3$=ME, X$_2$=(CH$_2$)xCON-(peptoid mixture)
X$_1$=X$_2$=ME, X$_3$=(CH$_2$)xCON-(peptoid mixture)

The above specific example has been put forth in order to demonstrate how peptoids of the invention can be used to form conjugates with pharmaceutically active drugs. However, it should be noted that the scope of the present invention is not restricted to any particular peptoid or peptoid mixture and is not restricted with respect to any particular effector compound such as any pharmaceutically active drug. Any drug which can be reacted with and covalently bound to a peptoid without a substantial effect on its pharmaceutical activity can be used in connection with the present invention.

The following specific examples are put forth so as to provide those of ordinary skill in the art with a complete disclosure and description of how to make the amino acid substitutes and peptoids of the invention as well as how to isolate desired bioactive peptoids from libraries produced. Accordingly, such examples are not intended to limit the scope of what the inventors regard as their invention. Efforts have been made throughout the examples to insure accuracy with respect to numbers used (e.g., amounts, temperature, pH, etc.) but some experimental errors and deviation should be accounted for. Unless indicated otherwise, parts are parts by weight, temperature is in degrees Centigrade, and pressure is at or near atmospheric.

EXAMPLES (Preparation of Monomers)

Representative monomers of the invention, suitable for peptide construction, were prepared as set forth below.

Example 1

FMOC-N-Benzylglycine

A. Reaction 1

N-benzylglycine ethyl ester (Aldrich, 4.0 mL, 20.9 mmol) was dissolved in methanol (40 mL) and treated overnight with aqueous KOH (10M, 8 mL) at room temperature. TLC indicated complete conversion to product. The solution was cooled in an ice bath and carefully acidified to pH 2 with HCl. White crystals were collected and recrystallized from aqueous methanol, to provide 3.95 g (93%) of the HCl salt.

B. Reaction 2

N-benzylglycine.HCl (1.07 g, 5.3 mmol) was dissolved in aqueous acetonitrile, and the pH brought to 9–10 with 1N NaOH. A solution of FMOC-Cl in acetonitrile was added dropwise, and the pH maintained by adding base, until the reaction was complete (as judged by TLC). The pH of the solution was lowered to 4, and the solution extracted with ethyl acetate. The organic layer was washed with water and dried over sodium sulfate. Silica gel chromatography (ethyl acetate/hexanes) yielded FMOC-N-benzylglycine as an oil (1.43 g, 70%), which could be recrystallized from acetic acid/methanol. This monomer may be used in peptides at any position at which an aromatic side chain is desired.

Example 1 Reaction Scheme

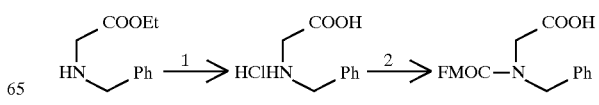

Example 2

FMOC-N-isobutylglycine

A. Reaction 3

Isobutylamine (50 mL, 0.5 mol) was cooled in an ice bath, and bromoacetic acid (6.1 g, 43.9 mmol) added slowly as a solid, insuring that each piece dissolved. After stirring overnight, the excess amine was removed and MeOH was added to the resulting oil. The resulting mixture was concentrated, and repeated using MeOH/HCl. Finally, a white solid was recrystallized from ethanol/ether to provide N-isobutylglycine.HCl (3.95 g, 53.7%).

B. Reaction 4

N-isobutylglycine.HCl (1.25 g, 7,46 mmol) was dissolved in aqueous acetonitrile and treated with FMOC-Cl as described in part (A) above. After the reaction was complete, the pH was lowered to 2.5 and the aqueous solution extracted with ethyl acetate. The organic layer was washed with water, saturated NaCl, and dried over sodium sulfate. Silica gel chromatography (ethyl acetate/hexanes) yielded FMOC-N-isobutylglycine as an oil (1.29 g, 47%). Additional material could be recovered from impure chromatographic fractions. This monomer may be used in peptides at any position at which an aliphatic, hydrophobic side chain is desired.

Example 2 Reaction Scheme

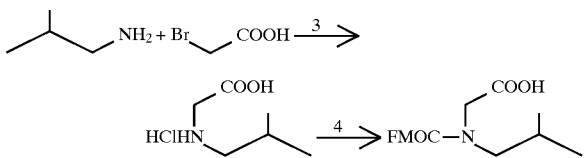

Example 3

FMOC-N-(N'-BOC-2-aminoethyl)glycine

A. Reaction 5

Ethylenediamine (65 mL, 0.97 mol) was cooled in an ice bath, and chloroacetic acid (10.0 g, 0.106 mol) added in small portions, allowing each portion to dissolve. After the addition was complete, the solution was allowed to stir overnight at room temperature. Water was added and the solution applied to a Dowex®-AG-1 column (OH⁻ form, 2.5×50 cm). The column was washed with water (2 L) until ninhydrin-negative, and the product eluted with 0.5N HOAc. The ninhydrin-positive fractions were pooled, concentrated, and recrystallized from EtOH/Et$_2$O/HCl to provide N-2-aminoethylglycine.HCl (9.7 g, 48%).

B. Reaction 6

N-2-aminoethylglycine.HCl (2.5 g, 13.1 mmol) was dissolved in water (20 mL) and dioxane (25 mL). The pH was brought to 11.2 with concentrated NaOH. BOC-nitrophenylcarbonate (3.5 g, 14.6 mmol) was dissolved in dioxane (20 mL) and added over 45 min with stirring, maintaining the pH with a pH stat. After the addition, the solution was stirred for one day at constant pH. Water was then added, the pH lowered to 6, and the resulting solution extracted with ether. The pH was further lowered to 3 with KHSO$_4$ and extracted with ether, then lowered to 2 and extracted with EtOAc. TLC indicated that the product remained in the aqueous layer. The product was used without further purification.

The pH of the solution was adjusted to 9.5 with NaOH, providing a total volume of about 200 mL. Acetone (50 mL) was then added, and FMOC-N-hydroxysuccinimide (4.64 g, 13.6 mmol) in acetone (100 mL) added dropwise while maintaining the pH. The reaction mixture was stirred overnight. The basic solution was extracted with ether and carefully acidified to pH 2.5 with HCl and KHSO$_4$. The acidic solution was washed with saturated NaCl and dried over sodium sulfate. After concentration, the solid was recrystallized from ethyl acetate/hexanes to provide FMOC-N-(N'-BOC-2-aminoethyl)glycine (4.74 g, 57% for two steps). This monomer may be used in peptides at any position at which a side chain containing basic side chain is desired.

Example 3 Reaction Scheme

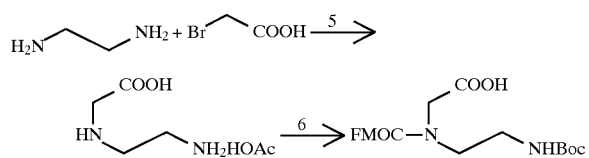

Example 4

FMOC-N-(2-t-butoxyethyl)glycine

A. Reaction 7

Ethanolamine (60 mL) was cooled in an ice bath, and chloroacetic acid (10.0 g, 10.5 mmol) added in portions, allowing each portion to fully dissolve. The solution was then heated to 60° C. for one hour. After cooling, the product was applied to a Dowex®-AG1 column (OH⁻ form, 2.5×50 cm). The column was washed with water until the washes were ninhydrin-negative, and the product eluted with 0.5N HOAc. After concentration, N-2(hydroxyethyl) glycine (9.8 g, 52%) was obtained.

B. Reaction 8

N-2(hydroxyethyl) glycine (5.18 g, 28.9 mmol) was dissolved in 1N NaOH (60 mL) and dioxane (60 mL). The pH was adjusted to 9.5 and the solution cooled in an ice bath. FMOC-Cl (10.0 g, 38.7 mmol) in dioxane (50 mL) was added dropwise with stirring while maintaining the pH by addition of NaOH. After the addition was complete, the solution was allowed to stir at room temperature for two more hours. The basic solution was extracted with ether. Then, the solution was carefully acidified to pH 2.5 with HCl, and the acidic solution extracted with EtOAc, which was washed with NaCl and dried over sodium sulfate. After concentration, the product was recrystallized from ethyl acetate/hexanes to provide FMOC-N-hydroxyethylglycine (9.11 g, 92%).

C. Reaction 9

The product (805 mg, 2.36 mmol) was dissolved in MeOH and the solution acidified with a few drops of H$_2$SO$_4$. The solution was heated at reflux for 30 minutes, until TLC indicated a complete conversion to product. Water was added, and the solution extracted with ether, ethyl acetate, and methylene chloride. The ether and ethyl acetate solutions were combined and washed with water and brine, and dried over sodium sulfate. The methylene chloride extract was washed with water and dried. The combined organic layers were concentrated to 880 mg of product, which was used without further purification. This product was dissolved in methylene chloride (11 mL) and cooled in a dry ice bath. Isobutylene (about 10 mL) was added, followed by concentrated sulfuric acid (100 μL). The flask was stoppered and allowed to stand at room temperature. After one week, the flask was cooled to −78° C., opened and allowed to warm up to room temperature under a stream of nitrogen. The methylene chloride solution was washed with sodium carbonate and water, and dried over sodium sulfate. The concentrated material was chromatographed using ethyl acetate/hexanes to provide two major products. NMR indicated one to be the desired product, with the produce apparently the bis t-butyl product.

The desired product (521 mg, 1.27 mmol) was suspended in 0.1M sodium phosphate (pH 8.0). Porcine liver esterase (100 μL, 108.5 u/mg, 10 mg/mL) was added followed by Triton® (200 μL, 10% aqueous solution). The pH was maintained at 8 by periodic addition of NaOH. After one day, the solution was extracted with ethyl acetate. TLC indicated a slower moving compound in addition to unreacted starting material, which was verified as FMOC-N-(2-t-butoxyethyl)glycine by NMR. This monomer may be used in peptides at any position at which a hydroxy-containing side chain is desired.

Example 4 Reaction Scheme

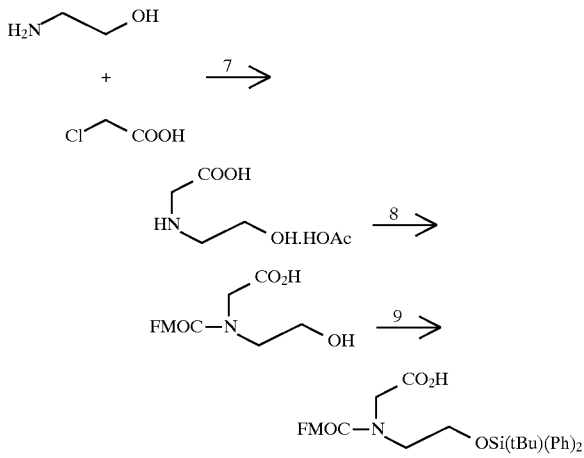

Example 5

FMOC-N-carboxymethyl(t-butyl ester)glycine

A. Reaction 10

Glycine, t-butyl ester (10.0 g, 52.3 mmol) was dissolved in water (150 mL) and the pH adjusted to 9.5 with NaOH. Chloroacetic acid (1.1 g, 11.6 mmol) in 50 mL water was added dropwise to the solution with stirring while maintaining the pH with a pH stat. After the addition was complete, the reaction was allowed to stir overnight. The basic solution was exhaustively extracted with EtOAc and $CH_2Cl_2$ until there was no additional glycine t-butyl ester in the aqueous layer, as judged by TLC. The material was used without further purification.

B. Reaction 11

The pH of the solution was adjusted to 9.5, and acetone (100 mL) added. A solution of FMOC-NHS (4.0 g, 11.9 mmol) in acetone (50 mL) was added slowly and the pH maintained at 9.5. After stirring 2 days, the basic solution was extracted with ether, cooled in an ice bath, and carefully acidified to pH 2.5 with $KHSO_4$. The acidic solution was extracted with ethyl acetate. The organic layer was washed with water and dried over sodium sulfate. After concentration, FMOC-N-carboxymethyl(t-butyl ester) glycine (3.07 g, 64% from chloroacetic acid) was obtained as an oil. This monomer may be used in peptides at any position at which an acidic side chain is desired.

Example 5 Reaction Scheme

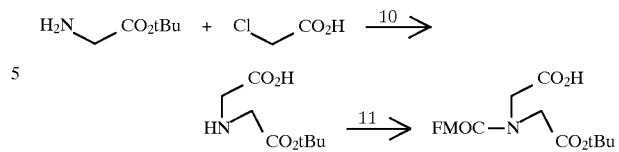

Example 6

Preparation of Peptides

Di- and tri-peptides containing 1–3 N-substituted glycine analogs of the invention were prepared using the N-substituted amino acids FMOC-N-iso-butylglycine (Leu*) and FMOC-N-benzylglycine (Phe*). The amino acids were loaded onto a Wang resin (S.-S. Wang, J Am Chem Soc (1973) 95:1328) and coupled using benzotriazoyloxy-tris(dimethylamino)phosphonium hexafluorophosphate (BOP) and diisopropylethylamine (DIEA). Substitution levels were determined using standard analytical procedures by quantifying the amount of FMOC released by treatment with piperidine in DMF. These resins are routinely capped with benzoyl chloride/pyridine prior to further coupling reactions.

HPLC analysis was performed using a Hewlett-Packard Diode-Array 1090 Liquid Chromatograph, using a 2% gradient of 0–100% acetonitrile (0.1% trifluoroacetic acid)/$H_2O$ (0.1% TFA) over 50 minutes, with an initial 5 min delay (flow rate 0.8 mL/min). The column used was a 40 mm×25 cm Vydac® C-18 stainless steel column. IR spectra were obtained using a Nicolet FT-IR. FMOC-amino acids, loaded resin, and BOP were obtained from Advanced Chemtech.

(A) FMOC-Leu*-Cl was prepared by dissolving FMOC-N-isobutylglycine (150 mg, 0.42 mmol) in $CH_2Cl_2$ (2.8 mL), and adding thionyl chloride (309 μL, 4.2 mmol) and 3 μL DMF (0.04 mmol). The reaction mixture was stirred for 5 hours and concentrated in vacuo, repeatedly dissolving in $CH_2Cl_2$ (3×) to provide FMOC-Leu*-Cl as a colorless oil (146 mg, 92%): IR ($cm^{-1}$)-1804, 1720, 1715. FMOC-Phe*-Cl was similarly prepared.

(B) The Wang resin (0.94 mmol/g, Applied Biosystems, Inc.) was loaded by combining FMOC-Phe* (0.8 mmol) with Wang resin (325 mg, 0.3 mmol) in $CH_2Cl_2$ (4.5 mL). BOP (267 mg, 0.6 mmol) was added and dissolved, followed by DIEA (265 μL, 1.5 mmol). The resulting slurry was stirred at 23° C. for 24 hours. The resin was then filtered and washed with $CH_2Cl_2$ and 40% MeOH/$CH_2Cl_2$, and dried under vacuum. The resin was then capped by swelling with $CH_2Cl_2$ (4.3 mL) and cooled to 0° C. Pyridine (120 μL) was added followed by benzoyl chloride (140 μL). The resin was stirred while warming to 23° C. over 1 hour, filtered and washed with $CH_2Cl_2$ and dried under vacuum to provide FMOC-Phe*-Wang.

(C) Similarly, proceeding as in part (B) above but substituting FMOC-N-isobutylglycine, FMOC-N-(N'-BOC-2-aminoethyl)glycine, FMOC-N-(2-t-butoxyethyl)glycine, or FMOC-N-carboxymethyl(t-butyl ester)glycine for FMOC-N-benzylglycine, the corresponding resins are prepared.

(D) FMOC-Phe*-Wang resin (63 mg, 0.43 mmol/g) was deprotected by initial washing with 20% piperidine in DMF, followed by treatment for 20 min. After repeatedly washing with DMF, MeOH, and $CH_2Cl_2$, the resin was treated with FMOC-Leu*-Cl (30 mg, 0.08 mmol) in $CH_2Cl_2$ (380 μL). Pyridine (110 μL, 1.4 mol) was added, and the resin shaken for 4 hours. Monitoring the coupling (A. Grandas et al., *Int J Peptide Protein Res* (1989) 33: 386–90) revealed that the reaction was complete within 20 min. Filtration and washing with $CH_2Cl_2$ and MeOH provided the fully coupled resin FMOC-Leu*-Phe*-Wang.

(E) Similarly, proceeding as in parts (B–D) above, the following resins (and their deprotected forms) were prepared:

FMOC-Leu*-Pro-Wang; FMOC-Leu*-Leu*-Wang;

FMOC-Leu*-Leu-Wang; FMOC-Phe*-Phe*-Wang;

FMOC-Gly-Leu*-Wang; FMOC-Leu*-Phe-Wang;

and FMOC-Leu*-Leu*-Phe-Wang.

Leu* indicates N-isobutylglycine, and Phe* indicates N-benzylglycine. The peptides are cleaved from the resins using 95% TFA, while the reaction was monitored by RP-HPLC as described above. The results were as follows:

TABLE 1

Peptides and Retention Times

| Peptide | Retention Time (min) |
|---|---|
| FMOC—Leu* | 38.7 |
| Leu* | (not retained) |
| FMOC—Phe* | 39.3 |
| Phe* | 15.0 |
| FMOC—Leu*—Leu* | 40.1 |
| Leu*—Leu* | 19.7 |
| FMOC—Leu*—Phe* | 41.1 |
| FMOC—Phe*—Phe* | 43.4 |
| FMOC—Leu*—Leu | 40.4 |
| Leu*—Leu | 21.9 |

Example 7

Solid Phase Chemistry

Resins: Unloaded WANG (HMP) resin, Rink resin, and preloaded PAM resins were bought from Advanced Chemtech or ABI. The first amino acid was coupled to the WANG and Rink resins using the PyBrop method described below.

Resin Deprotection: The resin was treated with a 20% piperidine in DMF solution for one minute, drained, and repeated for 20 m. After draining, the resin was washed with DMF 3 times and methylene chloride 5–7 times.

Substitution Level: A preweighed dried amount of resin is treated with a solution of 20% piperidine in DMF ($300\lambda$-1 mL) in an eppendorf tube on a vortexer. After 20–30 m, the tubes are centrifuged for a few minutes to settle the resin. An aliquot is removed ($50\lambda$) and diluted to 1 mL with acetonitrile. The absorbance at 300 nm is recorded vs. a standard of the same dilution pip/DMF in ACN. In general, the spectrum from 280–320 nm is taken to ensure the characteristic pattern for an FMOC derived product. The following formula is used to calculate the mmol/g (substitution level) of the resin:

$$\frac{\text{mmol}}{\text{g}} = \frac{[\text{Abs}(300 \text{ nm})][\lambda \text{ pip/DMF solution}][\text{ACN dilution}]}{[\text{mg resin}][\epsilon \text{ M}^{-1}\text{cm}^{-1}][1 \text{ cm}]}$$

e.g., 1.47 mg resin, $A_{300}$=0.298, 0.5 mL pip/DMF used, 50/1000 dilution gives:

$$\text{mmol/g} = \frac{[0.298][500][1000/50]}{[1.47][7040][1]} = 0.288 \text{ mmol/g}$$

Coupling

Acyl halide chemistry: The amino acid (1 mmol) was dissolved in methylene chloride (10 mL) and treated with thionyl chloride ($750\lambda$) and DMF ($10\lambda$). The reaction was monitored by TLC or HPLC by mixing $10\lambda$ with $100\lambda$ methanol. In all cases studied, the $R_f$ of the methyl ester was greater than the corresponding $R_f$ of the carboxylic acid. After stirring 30 m to 2 h, the solution was concentrated on a rotavap several times from methylene chloride, and benzene or toluene, followed by high vacuum concentration to remove the solvents. In general, the compounds were oils, and often colored yellow to brown. They were used without further purification. The acyl halide was dissolved in an appropriate amount of methylene chloride and was added to the deprotected resin, followed by a solution of DIEA/ methylene chloride. After an appropriate time, usually 1 hour, the resin was drained and washed well with methylene chloride, dried, and assayed for FMOC content.

PyBroP chemistry: The resin (~100 mg, 0.05 mmol), after deprotection, was washed well (5–10 times) with methylene chloride. A 0.2 mmol aliquot of the amino acid was weighted into a vial. This was dissolved in 1.0 mL methylene chloride and 0.1 mL DIEA. A 0.2 mmol aliquot of PyBroP (bromo-tris-pyrrolidino-phosphonium hexafluoro-phosphate), purchased from Nova chemicals UK, was weighted into another vial. It was also dissolved in 1.0 mL methylene chloride, however, this solution remained cloudy. The amino acid solution was added to the resin followed by the PyBroP solution. The mini-column was capped, vented, and gently shaken for one hour. The resin was drained, washed well with methylene chloride and ready for a repeat coupling or capping.

DIC/HOBt chemistry: The resin (~50 mg, 0.033 mmol), after deprotection, was washed well (5–10 times) with DMF. To the resin was added $440\lambda$ of DMF followed by $170\lambda$ of a 1M solution of amino acid in DMF and $170\lambda$ of a 1M solution of DIC and HOBt in DMF. The mini-column was capped, vented, and gently shaken for one hour. The resin was drained, washed well with methylene chloride and ready for a repeat coupling or capping.

Capping: After coupling, the resin was washed well with methylene chloride and treated with $100\lambda$ acetic anhydride, $100\lambda$ pyridine, and 2 mL methylene chloride for 30 minutes.

Example 8

Polymer Purification and Analysis

Polymers using WANG Resin: Polymers prepared using the WANG or RINK resins were cleaved using the standard protocol, i.e., 95% aqueous TFA for one hour at room temperature. No scavengers were necessary (no Trp, Tyr, Met). The TFA solution was filtered, dried down, and resuspended in 20% aqueous acetic acid for HPLC analysis.

Polymers using PAM Resin: Resins were cleaved in HF at 0° C. for one hour. Either the resin was extracted with DMF, or the resin was extracted with 50% aqueous acetic acid, concentrated, and redissolved in acetonitrile for HPLC analysis. In both cases, the organic solvent was diluted to approximately 25% with water before reversed phase HPLC on C-18 support.

Example 9

Proteolysis of Peptoids and Peptides

A peptide 6 mer of the sequence FMOC-LDFSKG-OH was prepared by conventional methods. The corresponding peptoid, FMOC-L*D*F*S*K*G-OH was prepared by the pybrop method listed above. Both compounds were purified to homogeneity by HPLC. Each substrate was dissolved to 0.5 mg/mL in 10% DMSO, 100 mM Tris, 100 mM CaCl$_2$, pH 8.0. Either trypsin or chymotrypsin was dissolved to 1 mg/mL in 0.001M HCl. At t=0, 10λ of enzyme or 0.001M HCl was added to 200λ of either the peptoid or peptide solution and incubated at 37° C. At the appropriate times, 50λ was removed and quenched with 50λ of 20% HOAc and assayed by HPLC on a C4 column with detection at 280 nm. The data below is given in percent area remaining on parent peak. Trypsin cleaved the peptide in only one place, and the cleavage was complete in 5 minutes. However, chymotrypsin had at least two cleavage sites, one preferential (cleavage ~60% completed after 10 minutes) and one not completely cleaved after three hours. The peptoid remained unchanged under all reaction conditions.

| % Area at 280 nm Remaining of Parent Peak by RP-HPLC | | | |
|---|---|---|---|
| | 5 min | 10 min | 3 hours |
| PEPTIDE | | | |
| Control | 100 | 100 | <100 |
| Trypsin | 0 | 0 | 0 |
| Chymotrypsin | 75 | 41 | 0 |
| PEPTOID | | | |
| Control | 100 | 100 | 100 |
| Trypsin | 100 | 100 | 100 |
| Chymotrypsin | 100 | 100 | 100 |

Example 10

Antibody Binding

Peptoids and peptides were prepared on the pins and tested under standard conditions. The assay is best interpreted qualitatively, and the chart below gives a summary of data from three antisera tested. They are representative for the twelve sera which gave signals with both the peptoids and peptides. A 'P' represents a peptide sequence which gave the highest 6–8 signals.

Likewise, a '*' represents a peptoid sequence which scored in the top 6–10. For the three sera tested, 33/120 sequences are represented which lends support to the premise that there is selective binding shown by the antibody.

| X-net table CONDENSED | | | | |
|---|---|---|---|---|
| No. in net | SERA Epitope: | S259-8 KDFL | S259-6 DFLEKI | S1400-44 saline-IgM |
| 3 | DFLKS | P | | |
| 4 | DFLSK | P | P | |
| 8 | DKFSL | | | P |
| 26 | FDKSL | | * | |
| 46 | FSKLD | | | P |
| 49 | KDFLS | P | P | |
| 57 | KFLDS | | | P |
| 59 | KFSDL | | | |
| 61 | KLDFS | | | * |
| 66 | KLSFD | | | *P |
| 67 | KSDFL | P | | |
| 72 | KSLFD | | | * |
| 77 | LDSFK | * | | |
| 81 | LFKDS | | P | |

| X-net table CONDENSED | | | | |
|---|---|---|---|---|
| No. in net | SERA Epitope: | S259-8 KDFL | S259-6 DFLEKI | S1400-44 saline-IgM |
| 87 | LKFDS | | | P |
| 88 | LKFSD | | | |
| 90 | LKSFD | | | *P |
| 92 | LSDKF | | * | |
| 98 | SDFLK | *P | P | |
| 101 | SDLFK | * | | |
| 102 | SDLKF | * | | |
| 103 | SFDKL | | * | |
| 104 | SFDLK | * | | |
| 105 | SFKDL | | * | |
| 107 | SFLDK | | P | |
| 109 | SKDFL | P | | |
| 113 | SKLDF | | | * |
| 114 | SKLFD | | | * |
| 116 | SLDKF | | * | |
| 117 | SLFDK | | | |
| 118 | SLFKD | | * | |
| 119 | SLKDF | | | * |
| 120 | SLKFD | | | * |

Example 11

Preparation of Effector Molecule Conjugate Library

A peptoid library may be prepared by immobilizing a set of peptoid monomers on an appropriate resin, dividing each batch of resin into a number of reaction mixtures equal to the number of different monomers to be added next, and addition of the monomers (one monomer to each "simultaneous" reaction mixture). The reaction products are then pooled, and again divided evenly into a number of reaction mixtures equal to the number of different monomers to be added in the third position, and the addition repeated. The cycle of separation into pools, addition of the next monomers, and recombination of some or all of the pools is repeated until polymers of the desired length are obtained. The result is a mixture of polymers of equal length, having every possible sequence of monomers represented in essentially equal amounts. A length of 2–8 monomers is preferred for this type of application. Provided each reaction is driven to completion, prior to mixing reaction products, and the mixture is equally divided by weight after each mixture is prepared, the final mixture will include each polymer in substantially equal molar amounts. Adjustments in weight amounts may be made to affect the amount of any polymer in the final product such that each polymer is not present in equal molar amounts but in different amounts, but in retrievable and analyzable amounts.

Peptoids of 2 or 3 monomers need not be recombined, but can be synthesized by automated methods to provide a set of N2 or N3 dimers or trimers, where N is the number of different monomers employed. Thus, a synthesis using 6 different monomers would provide 36 dimers, or 216 trimers. These oligomers could be assayed individually, or pooled into, e.g., pools of 6 polymers to form 6 pools of dimers or 36 pools of trimers followed by assay.

The compound 2,4-diamino-5-[3,5-di-methoxy-4-(3-hydrocarboxy-1-oxopropylamino)benzyl]pyrimidine is an effector molecule which exhibits inhibitory activity specific for the enzyme dihydrofolate reductase (DHFR) found in *Pneumocystis carinii* (the etiologic agent of pneumocystis carinii pneumonia, a leading cause of mortality in AIDS patients). 2,4-diamino-5-[3,5-dimethoxy-4-(3-hydrocarboxy-1-oxopropylamino)benzyl]pyrimidine is covalently linked to the peptoid library prepared above by esterification of the side chain carbonyl group to the carboxy terminus of the polymers, forming a library of effector molecule-polymer conjugates.

While the present invention has been described with reference to specific amino acids, amino acid substitutes and peptoids to describe specific embodiments, it should be understood by those skilled in the art that various changes can be made and equivalents can be substituted without departing from the true spirit and scope of the invention. In addition, many modifications may be made to adapt a particular amino acid substitute, peptoid or methodology for isolating bioactive peptoids to the object, spirit and scope of the present invention. All such modifications are intended to be within the scope of the claims appended hereto.

What is claimed:

1. A mixture of at least five non-homopolymeric polymers of differing sequences having a selected number of monomer units, said polymers selected from the group consisting of compounds of the general formula: $X_a$—(NR—$CH_2$—CO)$_n$—$X_b$, $X_a$—(O—CHR—CO)$_n$—$X_b$, $X_a$—(NH—CHR—CS)$_n$—$X_b$, $X_a$—(NOH—CHR—CO)$_n$—$X_b$, $X_a$—(O—CHR—$CH_2$—CO)$_n$—$X_b$, $X_a$—(NH—CHR—$CH_2$—$SO_2$)n—Xb, Xa—(NR—$CH_2CH_2$—$SO_2$)$_n$—$X_b$, $X_a$—(NR—$CH_2CH_2$—NHCO)$_n$—$X_b$ and $X_a$—(NR—$CH_2CH_2$—OCO)$_n$$X_b$, wherein, each R is a side chain which is independently alkyl of 2–6 carbon atoms, haloalkyl of 1–6 carbon atoms, alkynyl of 2–6 carbon atoms, cycloalkyl aryl of 6–10 carbon atoms, aryl-alkyl of 7–12 carbon atoms, substituted with 1–3 radicals independently selected from halo and nitro and hydroxy, aminoalkyl of 1–6 carbon atoms, hydroxyalkyl of 1–6 carbon atoms, carboxy, carboxyalkyl of 2–6 carbon atoms, carboalkoxy-alkyl of 3–10 carbon atoms, carbamyl, carbamylalkyl of 2–6 carbon atoms, guanidino, guanidinoalkyl of 1–6 carbon atoms, mercapto, mercaptoalkyl of 1–6 carbon atoms, alkylthioalkyl of 2–10 carbon atoms, imidazolyl, imidazolylalkyl of 4–10 carbon atoms, piperidyl, piperidylalkyl of 5–10 carbon atoms, indolyl, or indolylalkyl of 9–15 carbon atoms:

n is an integer from 2 to 50, inclusive; and $X_a$ and $X_b$ are each independently H, lower alkyl, lower aryl, aralkyl, lower acyl, a polypeptide of 1–100 amino acids, or an effector molecule capable of exhibiting biological activity.

2. The mixture of claim 1, wherein n is an integer from 5 to 20, inclusive.

3. The mixture of claim 1, wherein n is an integer from 5 to 10, inclusive.

4. The mixture of claim 1, wherein all of said polymers are compounds of the same general formula, and differ only by said side chains.

5. The mixture of claim 1, wherein said mixture comprises at least twenty non-homopolymeric polymers of differing sequence.

6. The mixture of claim 5, wherein said mixture comprises at least about fifty non-homopolymeric polymers of differing sequence.

7. The mixture of claim 6, wherein said mixture comprises at least two hundred non-homopolymeric polymers of differing sequence.

* * * * *